(12) United States Patent
Mascal

(10) Patent No.: US 7,829,732 B2
(45) Date of Patent: Nov. 9, 2010

(54) HIGH-YIELD CONVERSION OF CELLULOSIC BIOMASS INTO FURANIC BIOFUELS AND VALUE-ADDED PRODUCTS

(75) Inventor: Mark Mascal, Sacramento, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 12/404,828

(22) Filed: Mar. 16, 2009

(65) Prior Publication Data

US 2009/0234142 A1    Sep. 17, 2009

Related U.S. Application Data

(60) Provisional application No. 61/114,377, filed on Nov. 13, 2008, provisional application No. 61/037,294, filed on Mar. 17, 2008.

(51) Int. Cl.
*C07D 307/48* (2006.01)
(52) U.S. Cl. .................................................. 549/483
(58) Field of Classification Search .................. 549/483
See application file for complete search history.

(56) References Cited

U.S. PATENT DOCUMENTS

| 4,154,744 | A |   | 5/1979 | Hamada et al. |
| 4,335,049 | A |   | 6/1982 | Hamada et al. |
| 4,350,575 | A |   | 9/1982 | Porta et al. |
| 4,424,390 | A | * | 1/1984 | Hamada et al. ............. 549/483 |

FOREIGN PATENT DOCUMENTS

EP    1834950 A1    9/2007

OTHER PUBLICATIONS

Hawley's Condensed Chemical Dictionary 14th Edition, Richard J. Lewis Sr. editor, 2001, p. 901.*
Henry J. Horstman Fenton, "Derivatives of Methylfufural," LXXXV, Journal of Chemical Society: Transactions, vol. 79, Part 1, pp. 807-816.
Mildred Gostling, "XIX.-Note on the Action of Acids of Cellulose," 1903, J. Chem. Soc. Trans., 83, pp. 190-192.

* cited by examiner

*Primary Examiner*—Janet L Andres
*Assistant Examiner*—David E Gallis
(74) *Attorney, Agent, or Firm*—Townsend and Townsend and Crew LLP

(57) ABSTRACT

Paper, cotton, corn stover, straw, and wood are converted into furanic products in high yields (based on their cellulose content) using a simple, inexpensive process involving concurrent hydrolysis, dehydration, and substitution reactions coupled with continuous extraction into an organic phase. In a simultaneous process, the hemicellulose fraction of these substrates is converted into furfural, and together these constitute an efficient means for the total exploitation of the carbohydrate content of biomass.

16 Claims, 1 Drawing Sheet

US 7,829,732 B2

HIGH-YIELD CONVERSION OF CELLULOSIC BIOMASS INTO FURANIC BIOFUELS AND VALUE-ADDED PRODUCTS

CROSS-REFERENCES TO RELATED APPLICATIONS

This application claims the benefit of U.S. Provisional Application No. 61/037,294, filed Mar. 17, 2008, and U.S. Provisional Application No. 61/114,377, filed Nov. 13, 2008, each of which is incorporated by reference herein in their entirety.

STATEMENT AS TO RIGHTS TO INVENTIONS MADE UNDER FEDERALLY SPONSORED RESEARCH OR DEVELOPMENT

Not Applicable

BACKGROUND OF THE INVENTION

Automotive fuel production from biomass on any meaningful scale is largely limited in practice to the fermentative processing of either starch hydrolysates or sucrose to ethanol. Although cellulosic ethanol and biodiesel are alternatives to agriculturally-derived ethanol, there are limitations associated with their use. A key issue in the case of cellulosic ethanol is the difficult and expensive derivation of fermentable sugars from lignocellulosic biomass. Beyond this, there are the limitations inherent in the fermentation process in terms of rate, efficiency, and the cost of isolating pure ethanol from a dilute aqueous solution. Additionally, ethanol is volatile, toxic, hydrophilic, potentially corrosive to engine components, and of relatively low energy content compared to gasoline or diesel fuel.

Furan-based biofuels, such as those produced from cellulose, are an alternative to ethanol as a biofuel. Cellulose has been used to produce ethanol, but can also be used to prepare furanic biofuels by way of 5-(chloromethyl)furfural (CMF). CMF can be converted into 5-(ethoxymethyl)furfural (EMF) by mixing with ethanol. EMF is already being commercially developed as a promising diesel fuel additive. Alternatively, hydrogenolysis of the halogen in CMF gives 5-methylfurfural (MF), an attractive biofuel candidate, since only 2 g of $H_2$ are required for the synthesis of 110 g of MF, as opposed to 46 g of ethanol in the synthesis of 154 g of EMF.

CMF was described as early as 1901 as a product from the action of dry hydrogen chloride on cellulose. While the conversion for this reaction was low (12%), a related study in which anhydrous HBr was employed showed that the bromo analogue of CMF could be produced from cellulose in up to 48% yield, although glucose itself underwent the reaction in only 11% yield. A number of additional reports address the preparation of CMF from fructose, which is consistent with the related, facile conversion of fructose into 5-(hydroxymethyl)furfural (HMF). Fructose is expensive and is not considered a viable feedstock for biofuel or value added product synthesis.

Substituted furans and their derivatives, such as HMF, furfural, and levulinic acid, are also important value-added products, and are used as feedstocks for the production of resins, polymers, and chemical intermediates of use to commodity industries, such as the healthcare, cosmetic, materials, and foodstuff industries.

Other furan products, such as furfural, can be prepared from hemicellulose. Hemicellulose is the second most abundant organic material in nature, representing 25-35% of lignocellulose by mass (*J. Ind. Microbiol. Biotechnol.* 2003, 30, 279). In mainstream ethanol production, hemicellulose goes unutilized, since conventional yeasts cannot ferment $C_5$ sugars. Although work both with native and recombinant microorganisms has led to strains that can utilize xylose (the most abundant pentose in hemicellulose), limitations in rate, yield, stability, and inhibitor tolerance have presented obstacles to industrial applications of this technology (*Adv. Biochem. Engin. Biotechnol.* 2007, 108, 179; *Adv. Biochem. Engin. Biotechnol.* 2007, 108, 147; *Biotech Adv.* 2007, 25, 425; *Appl. Microbiol. Biotechnol.* 2007, 74, 937).

What is needed is a process for preparing CMF, furfural, and associated furanic products, in high yields from biomass such as cellulose and hemicellulose containing materials. Surprisingly, the present invention meets this and other needs.

BRIEF SUMMARY OF THE INVENTION

In one embodiment, the present invention provides a method for preparing 5-(chloromethyl)furfural (CMF), or a derivative thereof, in greater than 50% yield. The method includes contacting a saccharide, an aqueous acid, an inorganic salt and an organic solvent in a reaction vessel at a temperature of from about 30° C. to about 100° C., such that CMF is produced. The method also includes removing the organic solvent to an isolation vessel, such that any CMF dissolved in the removed organic solvent is collected in the isolation vessel. The method also includes adding additional organic solvent to the reaction vessel. The removing and adding steps of the method are performed continuously, thereby preparing CMF, or a derivative thereof, in greater than 50% yield from the saccharide.

In another embodiment, the present invention provides a method for preparing 5-(chloromethyl)furfural (CMF), or a derivative thereof, in greater than 50% yield. The method includes contacting cellulose, concentrated hydrochloric acid, lithium chloride and 1,2-dichloroethane in a reaction vessel at a temperature of about 65° C., such that a biphasic mixture is formed, wherein CMF is produced. The cellulose, concentrated hydrochloric acid, and lithium chloride form an aqueous layer and the 1,2-dichloroethane forms an organic layer. The method also includes removing the 1,2-dichloroethane to an isolation vessel, such that any CMF dissolved in the removed 1,2-dichloroethane is collected in the isolation vessel. The method also includes adding the removed 1,2-dichloroethane to the reaction vessel as additional 1,2-dichloroethane, such that the CMF in the isolation vessel remains in the isolation vessel. The contacting, removing and adding steps of the method are performed continuously, thereby preparing CMF, or a derivative thereof, in greater than 50% yield from the saccharide.

DETAILED DESCRIPTION OF THE INVENTION

I. General

Figure 1:
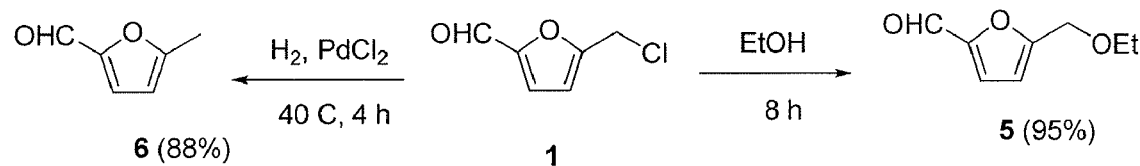
FIG. 1 shows the conversion of 5-(chloromethyl)furfural (CMF, 1) to 5-(ethoxymethyl)furfural (EMF, 5) by reaction with ethanol, and to 5-methylfurfural (MF, 6) by hydrogenation.

Glucose, sucrose, and microcrystalline cellulose can be individually converted into a mixture of 5-(chloromethyl) furfural (CMF, 1), 5-(hydroxymethyl) furfural (HMF, 2), 2-(2-hydroxyacetyl)furan (HAF, 3) and levulinic acid (LA, 4) in total isolated yields of up to 90% by reaction with an aqueous HCl—LiCl solution.

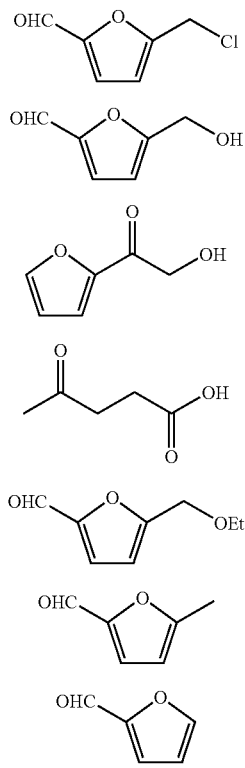

Cellulose is converted into furanic products in isolated yields of greater than 80% by conversion mainly into 5-(chloromethyl)furfural (CMF, 1), a hydrophobic molecule which can be sequestered into organic solvents in a two-phase reaction medium. The experimental setup used to this purpose is an apparatus for continuous extraction of an aqueous solution with a solvent of greater density than water.

The method of the present invention involves preparing CMF in greater than 50% chemical yield. The first step of the method involves contacting cellulose, concentrated hydrochloric acid, lithium chloride and 1,2-dichloroethane (DCE) in a reaction vessel at a temperature of about 65° C. The combination of these reagents forms a biphasic mixture with the cellulose, concentrated hydrochloric acid and lithium chloride forming an aqueous layer and the DCE forming a heavier than water organic layer. Heating this mixture forms CMF which is then extracted from the aqueous layer and into the DCE organic layer at the interface of the biphasic mixture. The DCE can be continuously removed to an isolation vessel. The DCE that is removed from the reaction vessel can be replaced continuously with additional DCE that can be fresh DCE or DCE recycled from the isolation vessel. The DCE can be recycled by a variety of methods, for example, recycling of the DCE in the isolation vessel can involve heating the isolation vessel to reflux the DCE, which is then condensed and directed into the reaction vessel. Alternatively, the DCE containing the CMF is directed into a vacuum evaporator, and the DCE is condensed and then introduced back into the biphasic reactor. Isolated CMF remains in the isolation vessel when the DCE is recycled. When the DCE, whether fresh or recycled, is added to the reaction vessel, the DCE passes through the aqueous layer and extracts CMF from the aqueous layer and into the DCE. Additional DCE is removed, and the process repeated. The steps of the method can be performed continuously and simultaneously, thereby preparing CMF, or a derivative thereof, in greater than 50% chemical yield from the saccharide.

CMF can be converted to high energy fuels by reaction with ethanol to prepare 5-(ethoxymethyl)furfural (EMF, 5), or by hydrogenation to prepare 5-methylfurfural (MF, 6). Furfural (7) can also be prepared by the method of the present invention from starting material which also contains $C_5$ sugars (pentose sugars), such as those found in hemicellulose, which is a component of cellulosic biomass. Other high energy fuels can be prepared by reaction of CMF with other alcohols, such as methanol, propanol, n-butanol and isobutanol.

II. Definitions

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

As used herein, the term "saccharide" refers to a sugar, such as a monosaccharide, a disaccharide, an oligosaccharide or a polysaccharide. Monosaccharides include, but are not limited to, glucose, ribose and fructose. Disaccharides include, but are not limited to, sucrose and lactose. Polysaccharides include, but are not limited to, cellulose, hemicellulose and lignocellulose or starch. Other saccharides are useful in the present invention.

As used herein, the term "cellulose" refers to a homopolymer of $\beta(1\rightarrow4)$ linked D-glucose units that form a linear chain and has the following structure:

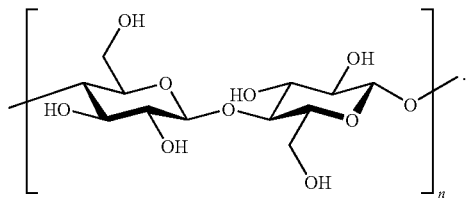

Cellulose can contain several hundred to several thousand or more glucose units, making cellulose a polysaccharide. Cellulose is found in many natural products, such as the cell walls of plants, and thus can be found in wood, pulp and cotton, among others.

As used herein, the term "hemicellulose" refers to a heteropolymer containing different saccharide units, such as, but not limited to, xylose, mannose, galactose, rhamnose and arabinose. Hemicellulose forms a branched polymer with several hundred to several thousand sugar units. Hemicellulose can include both pentose and hexose sugars.

As used herein, the term "lignocellulose" refers to plant biomass that includes cellulose, hemicellulose and lignin.

As used herein, the term "biomass" refers to material that includes cellulose and/or hemicellulose. Biomass includes, but is not limited to, wood residue, paper waste (such as from a municipality), agricultural residue (such as plant waste), and energy crops.

As used herein, the term "reaction vessel" refers to a vessel for conversion of the saccharide, such as cellulose, to CMF. The reaction vessel includes an outlet for the organic solvent to transfer to the isolation vessel. The reaction vessel can also include an inlet for organic solvent to enter the reaction vessel from the isolation vessel or from another source. The reaction vessel can be made of a variety of materials, such as glass and metal, to tolerate the reaction conditions. For example, the reaction vessel can be made of pyrex.

As used herein, the term "isolation vessel" refers to a vessel for isolation and collection of the CMF from the reaction vessel. The isolation vessel has at least one inlet/outlet that allows organic solvent from the reaction vessel to enter the isolation vessel and, in some embodiments, allows vapor phase organic solvent to exit the isolation vessel and re-enter the reaction vessel following condensation of the organic solvent. The isolation vessel can be made of a variety of materials, such as glass and metal, to tolerate the reaction conditions. For example, the isolation vessel can be made of pyrex.

As used herein, the term "organic solvent" refers to a solvent that is generally immiscible with water, such as non-polar and polar aprotic solvents. Organic solvents useful in the present invention can be more dense than water or less dense than water. Organic solvents include, but are not limited to, diethyl ether, diisopropyl ether, ethyl acetate, pentane, hexane, heptane, cyclohexane, benzene, toluene, as well as halogenated solvents such as chloroform, dichloromethane, carbon tetrachloride, 1,2-dichloroethane, and 1,1-dichloroethane. Other organic solvents are useful in the present invention.

As used herein, the term "aqueous acid" refers to an acid dissolved in water. Aqueous acids useful in the present invention include, but are not limited to, hydrochloric acid (HCl), hydrobromic acid (HBr), nitric acid, phosphoric acid, sulfuric acid, and fluoboric acid. The aqueous acids can have any suitable concentration in water, for example, the aqueous acid can be concentrated, such as concentrated hydrochloric acid.

As used herein, the term "inorganic salt" refers to a complex of a positively charged species and a negatively charged species where neither species includes the element carbon. Each positively and negatively charged species can be an element or a collection of elements, such as a mineral. Examples of inorganic salts useful in the present invention include, but are not limited to, lithium salts, such as lithium chloride (LiCl), magnesium salts, such as magnesium chloride ($MgCl_2$), calcium salts, such as calcium chloride ($CaCl_2$). Other salts are also useful, such as silicate, carbonate, sulfate, oxide, sulfide, phosphate, or perchlorate salts.

As used herein, the term "immiscible" refers to one solvent having poor solubility in another solvent. For example, a first solvent is immiscible in a second solvent when less than 10 g of the first solvent will dissolve in about 100 g of the second solvent. In the instant method, the organic solvent is immiscible in water.

As used herein, the term "continuously" refers to the steps of the method of the present invention being practiced without substantial interruption or break, but not necessarily constantly. For example, the steps of the method can be performed constantly throughout the duration of the method. Alternatively, the addition and removal steps of the present invention can be performed several times throughout the duration of the process of the present invention at a variety of intervals. The interval can be on the scale of minutes, hours or days.

As used herein, the term "yield" refers to the chemical yield of the product from the starting saccharide. The chemical yield can be provided in units of grams or moles, but is always based on the amount of starting saccharide. Because the biomass starting material for the method of the present invention can include components other than saccharides, the chemical yield is not necessarily calculated based on the amount of biomass used for the starting material. Rather, the amount of saccharide in the starting material is used to determine the chemical yield of the CMF, and other furanic products.

III. Method of Preparing 5-(chloromethyl)furfural (CMF)

The present invention provides a method for the preparation of a liquid fuel precursor and value-added chemical intermediate from biomass such as cellulose, hemicellulose and lignocellulose. When the biomass contains cellulose, the cellulose is hydrolyzed to glucose under the reaction conditions, followed by the dehydration of glucose to 5-(hydroxymethyl)furfural (HMF). The HMF hydroxy group is then substituted under the reaction conditions with chloride to afford 5-(chloromethyl)furfural (CMF). The method involves reacting the biomass with a strong acid such as hydrochloric acid, in the presence of an inorganic salt such as lithium chloride (LiCl), above room temperature in order to prepare CMF. The CMF product can be removed from the reaction mixture by a variety of methods, including periodic removal or via constant liquid-liquid extraction using an organic solvent in order to minimize side reactions and decomposition of CMF. The biomass, strong acid and inorganic salt form an aqueous layer or suspension, and the organic solvent forms an organic layer. The organic solvent extracts the CMF at the interface of the organic layer and aqueous layer, as well as by organic solvent passing through the aqueous layer. When the biomass includes pentose sugars, such as when the biomass includes hemicellulose, furfural is also formed using the method of the present invention.

In some embodiments, the present invention provides a method for preparing CMF, or a derivative thereof, in greater than 50% chemical yield. The method involves contacting a saccharide, an aqueous acid, an inorganic salt and an organic solvent in a reaction vessel at a temperature from about 30° C. to about 100° C., such that CMF is produced. The method also involves removing the organic solvent to an isolation vessel, such that any CMF dissolved in the removed organic solvent is collected in the isolation vessel. The method also involves adding additional organic solvent to the reaction vessel. The removing and adding steps are performed continuously such that CMF, or a derivative thereof, is prepared in greater than 50% chemical yield from the saccharide.

The saccharide used in the present invention can be any saccharide or saccharide-containing substance. The saccharide can be a single saccharide or a mixture of saccharides, such as fructose, glucose, ribose, or sucrose, among others. The saccharide can be a monosaccharide, disaccharide, oligosaccharide, or polysaccharide, or a combination thereof. Monosaccharides useful in the method include, but are not limited to, glucose, fructose and ribose. Disaccharides useful in the method include, but are not limited to, sucrose, maltose and lactose. Polysaccharides include, but are not limited to, cellulose, hemicellulose and lignocellulose or starch. The saccharides can be synthetic or naturally occurring, such as from plant biomass. The saccharides can also be modified, such as by forming esters, or with N-acetyl groups.

Saccharide-containing biomass can include agricultural waste such as corn stover, corn cobs, wheat or oat straw, silage, etc. Biomass that is useful in the method includes municipal waste, paper products, paper waste, wood residue, agricultural residue (such as plant waste), and energy crops. Forestry waste can include leaves, pine needles, branches, fallen or diseased trees, brush, etc. Domestic waste can include newspaper or other waste paper, waste foodstuffs, vegetation, or processed municipal solid waste from landfills and dump sites. Other saccharides and biomass sources are known to one of skill in the art.

When biomass is used as the source of the saccharide, the biomass can be mechanically processed prior to use in the method of the present invention. For example, filter paper, cotton and newsprint can be cut into pieces of about 2.5-5 mm. Wood can be reduced to sawdust and ball milled to a powder. Corn stover and wheat straw can each be cut into pieces of about 1-2 cm and ball milled to a powder.

In some embodiments, the saccharide includes a polysaccharide. In other embodiments, the polysaccharide includes at least one of cellulose, hemicellulose and starch or lignocellulose. In some other embodiments, the polysaccharide includes cellulose. In still other embodiments, the polysaccharide includes hemicellulose. In yet other embodiments, the saccharide is obtained from biomass. In still yet other embodiments, the saccharide includes a monosaccharide. In another embodiment, the saccharide includes a disaccharide.

The saccharide can be present in any useful concentration in the method of the present invention. For example, the saccharide can be present from about 0.1% to about 50% (w/w) of the aqueous layer.

The aqueous acid of the method can be any acid in water. Acids useful in the method include, but are not limited to, hydrochloric acid (HCl), hydrobromic acid (HBr), nitric acid, phosphoric acid and sulfuric acid. The acid can also be a chloride acid, or an acid having a chloride anion. For example, the acid can be hydrochloric acid. The acid can be of any useful concentration in water. For example, when the acid is hydrochloric acid, concentrated hydrochloric acid (37% (w/w) in water) can be used in the method of the present invention.

The inorganic salt of the method can be any inorganic salt. The cation of the inorganic salt can be an alkali metal, an alkali earth metal, a transition metal, a post-transition metal, a lanthanide or an actinide. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. Post-transition metals include Al, Ga, In, Tl, Ge, Sn, Pb, Sb, Bi, and Po. The anion of the inorganic salt can be any element of the periodic table capable of forming an anion, such as, but not limited to, halogens (F, Cl, Br, I and At) as well as other nonmetals (N, O, P, S and Se). The anion can also be a mineral, such as a silicate, carbonate, sulfate, oxide, sulfide, phosphate, perchlorate, among others. For example, the inorganic salt can be lithium chloride (LiCl). The inorganic salt can also be $MgCl_2$, $ZnCl_2$, NaCl or KCl.

The inorganic salt can be present in any useful concentration in the method of the present invention. For example, the inorganic salt can be present from about 0.1% to about 50% (w/w) of the aqueous layer. The inorganic salt can also be present in a range from about 1% to about 10% (w/w). The inorganic salt can also be present in an amount of about 5% (w/w).

The organic solvent of the method can be any solvent that is poorly miscible (soluble) with water. For example, the organic solvent can have a solubility in water of less than about 10 g per 100 g of water. Organic solvents useful in the present invention can be more dense than water or less dense than water. Organic solvents include, but are not limited to, diethyl ether, diisopropyl ether, ethyl acetate, pentane, hexane, heptane, cyclohexane, benzene, toluene, as well as halogenated solvents such as chloroform, dichloromethane, carbon tetrachloride, 1,2-dichloroethane, and 1,1-dichloroethane. The organic solvent can be more dense than water, or less dense than water. The organic solvent can be 1,2-dichloroethane (DCE). Other organic solvents are useful in the method of the present invention.

The method of the present invention can be carried out at any suitable temperature. For example, the temperature can be from about room temperature to about the boiling point of water, 100° C. Other useful ranges for the temperature include from about 50° C. to about 80° C. Still other useful ranges for the temperature include from about 60° C. to about 70° C. One of skill in the art will appreciate that other temperature ranges are useful in the present invention.

The method of the present invention can be carried out at any suitable pressure. For example, the pressure can be from about 0.1 atm, or less, to about 10 atm, or more. In some instances, the pressure is about atmospheric pressure.

The method of the present invention can also include other components and reagents known to one of skill in the art. For example, other components and reagents can include buffers, surfactants, additional salts, and additional solvents.

The method of the present invention can provide CMF in at least 50% chemical yield. For example, the yield can be at least 60%, 70%, 80%, or 90%, based on the saccharide content of the starting material. In addition to CMF, the process of the present invention also provides 5-(hydroxymethyl)furfural (HMF), 2-(2-hydroxyacetyl)furan (HAF) and levulinic acid (LA). The yield of total organic content (CMF, HMF, HAF and LA, and other products such as furfural) can be at least 75%, 80%, 85%, or 90%, based on the saccharide content of the substrate. In some embodiments, the method prepares 5-(hydroxymethyl)furfural (HMF), 2-(2-hydroxyacetyl)furan (HAF) and levulinic acid (LA) such that the total yield of CMF, HMF, HAF and LA is at least 75% based on the saccharide content.

The removing and adding steps can be performed at a variety of intervals during the course of the process of the present invention. For example, the interval between repeating the removing and adding steps can be 1, 5, 10, 15, 20, 25, 30, 35, 40, 45, 50, 55 or 60 minutes. Alternatively, the interval can be 1, 2, 3, 4, 5, 6, 7, 8, 9, 10, 11, or 12 hours. In some embodiments, the steps of the process are practiced constantly.

The additional organic solvent of the present invention can be new organic solvent that is added to the reaction vessel, or can be the removed organic solvent from the isolation vessel that is recycled back into the reaction vessel. When the additional organic solvent is the removed organic solvent, the CMF collected in the isolation vessel remains in the isolation vessel.

The method of the present invention can be carried out in any suitable apparatus for continuous liquid-liquid extraction. For example, the apparatus can include a reaction vessel that into which is added the saccharide, the aqueous acid, the inorganic salt and the organic solvent. When the organic solvent is more dense than water, the reaction vessel includes a tube at the bottom that connects to an isolation vessel containing more organic solvent. When the organic solvent is less dense than water, the reaction vessel includes a tube connected to the reaction vessel on the side wall. In one embodiment, the isolation vessel is heated to the proper temperature to boil the organic solvent. The isolation vessel is also attached to a condenser such that organic solvent that is boiled in the isolation vessel condenses, enters the reaction vessel, passes through the aqueous layer extracting any CMF, or other products as described within, becomes part of the organic layer and is then isolated in the isolation vessel. Thus, when the reaction vessel is heated at a temperature such as from about 60° C. to about 70° C., the saccharide is converted into CMF (and other furanic products such as furfural when pentose sugars are present), and the organic solvent extracts the CMF from the aqueous layer. The organic solvent of the reaction vessel travels from the reaction vessel into the isolation vessel, where the organic solvent is boiled, condensed, and directed back to the reaction vessel. CMF and other products, however, remain in the isolation vessel. Thus, by the method of the present invention, CMF and furfural, as well as other products, can be prepared by simultaneously converting saccharide to CMF, removing the organic solvent to concentrate the CMF, and other products, in the isolation vessel, and returning the organic solvent to the reaction vessel.

Apparatus suitable for the method of the present invention is known to one of skill in the art. For example, the apparatus can be glass, such as pyrex, or metal. Commercial apparatus are available from ChemGlass, Aldrich, Kontes, Synthware, and others.

In some embodiments, the present invention provides a method for preparing 5-(chloromethyl)furfural (CMF), or a derivative thereof, in greater than 50% chemical yield. The method involves contacting cellulose, concentrated hydrochloric acid, lithium chloride and 1,2-dichloroethane in a reaction vessel at a temperature of about 65° C., such that a biphasic mixture is formed, wherein CMF is produced. The cellulose, concentrated hydrochloric acid, and lithium chloride form an aqueous layer and the 1,2-dichloroethane forming an organic layer. The method also includes removing the 1,2-dichloroethane to an isolation vessel, such that any CMF dissolved in the removed 1,2-dichloroethane is collected in the isolation vessel. The method also includes adding additional 1,2-dichloroethane to the reaction vessel, such that the additional 1,2-dichloroethane passes through the aqueous layer and extracts additional CMF into the isolation vessel, whereby the CMF remains in the isolation vessel. The contacting, removing and adding steps of the method are performed continuously, thereby preparing CMF, or a derivative thereof, in greater than 50% chemical yield from the saccharide.

IV. Biofuel Preparation

The product of the method of the present invention, CMF, can be reacted with a variety of reagents to provide other compounds useful as a fuel or fuel precursor. For example, CMF can be reacted with a nucleophile to displace the chlorine atom. The nucleophile can be any suitable nucleophile, such as water, alcohols, and hydride, among others. When the nucleophile is water, 5-(hydroxymethyl)furfural (HMF, 2) can be formed. When the nucleophile is an alcohol, such as ethanol, 5-(ethoxymethyl)furfural (EMF, 5) can be formed. When the chlorine is replaced with hydrogen, the hydrogen can be molecular hydrogen used in conjunction with a hydrogenation catalyst such as $PdCl_2$.

EMF, a liquid with a boiling point of 235° C., is considered to be a promising alternative fuel, the energy density of which is 30.3 MJ $L^{-1}$, substantially higher than that of ethanol (23.5 MJ $L^{-1}$), and comparable to that of standard gasoline (31.1 MJ $L^{-1}$) and diesel fuel (33.6 MJ $L^{-1}$).

Other biofuel products and precursors can also be prepared from the method of the present invention. For example, when the saccharide includes hemicellulose, furfural (7) can be prepared from the $C_5$ sugars of the hemicellulose. Moreover, the method can prepare HMF concurrently with the preparation of CMF.

The energy density of EMF, 5-methylfurfural (MF, 6), and furfural, in comparison to standard automotive fuels and ethanol, are shown below (Table 1). As can be seen, EMF possesses >97% of the energetic value of standard gasoline. Furfural, although not typically considered for use directly in fuels, is also a highly energetic liquid. Even MF, while only 83% as energetic as gasoline, is still a potentially better fuel than ethanol in terms of energy density.

TABLE 1

Measured heats of combustion.

| compound | $\Delta Hc \pm \sigma$ (kJ $L^{-1}$) |
|---|---|
| diesel fuel | 33,602 ± 90 |
| gasoline[a] | 31,181 ± 58 |
| EMF | 30,332 ± 180 |
| furfural | 28,175 ± 171 |
| MF | 25,905 ± 102 |
| ethanol | 23,547 ± 107 |
| cellulose | 15,823 ± 73[b] |

[a]Regular grade, 87 octane.
[b]$\Delta Hc$ value in kJ $kg^{-1}$.

Other products can be prepared from CMF prepared by the method of the present invention. For example, HMF can be prepared by reaction of CMF with water to substitute the chlorine with a hydroxy group. Levulinic acid can be prepared by reaction of CMF with water under acidic conditions. Levulinic acid esters can be prepared by reaction CMF with a suitable alcohol.

V. Examples

Example 1

Preparation of 5-(chloromethyl)furfural from biomass

Filter paper, cotton, and newsprint separately were cut into 0.25-1 $cm^2$ pieces; wood (birch) was reduced to sawdust and then ball milled to a powder; corn stover was cut into 1-2 cm pieces and the resulting material was ball milled to a powder; wheat straw was cut to 1-2 cm pieces and internodes were removed. The resulting material was then ball milled to a powder.

Samples of biomass, mechanically processed as described above, were introduced into concentrated HCl (75 mL) with stirring at room temperature over the course of 1-2 min. The mixture became homogeneous after an additional 5-10 min stirring, and was introduced into the reaction chamber. LiCl (10 g) was dissolved in small portions in a second aliquot of concentrated HCl (75 mL) over the course of 5 minutes, and this solution was also added to the reaction chamber. A boiling flask containing 1,2-dichloroethane (150 mL) and anhydrous sodium sulfate drying agent was attached to the apparatus and the solvent was heated to reflux. The aqueous slurry was heated at 65° C. with continuous mechanical stirring and subjected to continuous extraction for 18 h. At this point, further LiCl (5 g) in concentrated hydrochloric acid (75 mL) was added to the extraction chamber and extraction was continued for another 12 h. During the extraction the boiling flask was emptied every 6 h and replaced with fresh 1,2-dichloroethane (150 mL) and sodium sulfate drying agent. The combined organic extracts were distilled to recover the solvent, and the residual oil was chromatographed (silica gel, $CH_2Cl_2$: $Et_2O$, 2:1→$CH_2Cl_2$:MeOH, 95:5 gradient) to give 5-(chloromethyl)furfural (CMF, 1) $^1$H NMR ($CDCl_3$); 4.36 (s, 2H), 6.32 (d, 1H), 6.95 (d, 1H), 9.25 (s, 1H), $^{13}$C NMR ($CDCl_3$); 36.1, 111.6, 122.1, 152.2, 155.3, 177.1; 5-(hydroxymethyl) furfural (HMF, 2), $^1$H NMR ($CDCl_3$); 3.51 (brs, 1H), 4.66 (s, 2H), 6.50 (d, 1H), 7.21 (d, 1H), 9.51 (s, 1H), $^{13}$C NMR 8 ($CDCl_3$); 56.9, 110.1, 123.9, 151.8, 162.0, 178.1; 2-(2-hydroxyacetyl)furan (HAF, 3), $^1$H NMR ($CDCl_3$); 3.26 (br s, 1H), 4.71 (s, 2H), 6.56 (t, 1H), 7.26 (d, 1H), 7.60 (d, 1H), $^{13}$C NMR ($CDCl_3$); 65.2, 112.7, 118.0, 147.2, 150.3, 187.8; levulinic acid (LA, 4), $^1$H NMR ($CDCl_3$); 2.17 (s, 3H), 2.59 (t, 2H), 2.73 (t, 2H), $^{13}$C NMR ($CDCl_3$); 27.9, 29.9, 37.8, 178.2, 207.0; and furfural (7), $^1$H NMR ($CDCl_3$); 6.63 (m, 1H), 7.30 (m, 1H), 7.73 (m, 1H), 9.66 (s, 1H), $^{13}$C NMR ($CDCl_3$); 112.8, 121.5, 148.3, 153.1, 177.9.

Example 2

Conversion of Cellulose into Furanic Products 1,2-Dichloroethane (500 mL) was introduced into the extraction chamber of a standard apparatus for continuous extraction with a solvent heavier than water. A homogeneous suspension of microcrystalline cellulose (2.05 g, 5% water by mass) was prepared in a solution of lithium chloride (10 g) in concentrated hydrochloric acid (150 mL), and this was added to the extraction chamber. A boiling flask containing 1,2-dichloroethane (150 mL) and anhydrous sodium sulfate was attached to the apparatus and the solvent was heated to reflux. The aqueous slurry was heated at 65° C. with continuous mechanical stirring and subjected to continuous extraction for 18 h. At this point, further LiCl (5 g) in concentrated hydrochloric acid (75 mL) was added to the extraction chamber and extraction was continued for another 12 h. During the extraction the boiling flask was emptied every 6 h and replaced with fresh 1,2-dichloroethane (150 mL). The combined organic extracts were distilled to recover the solvent, and the residual oil (1.469 g) was chromatographed (silica gel, $CH_2Cl_2$:$Et_2O$, 2:1 gradated to $CH_2Cl_2$:MeOH, 95:5) to give 5-(chloromethyl)furfural (CMF, 1) (1.233 g, 71%), $^1$H NMR ($CDCl_3$); 4.36 (s, 2H), 6.32 (d, 1H), 6.95 (d, 1H), 9.25 (s, 1H), $^{13}$C NMR ($CDCl_3$); 36.1, 111.6, 122.1, 152.2, 155.3, 177.1; 2-(2-hydroxyacetyl)furan (HAF, 3) (0.116 g, 8%), $^1$H NMR ($CDCl_3$); 3.26 (brs, 1H), 4.71 (s, 2H), 6.56 (t, 1H), 7.26 (d, 1H), 7.60 (d, 1H), $^{13}$C NMR ($CDCl_3$); 65.2, 112.7, 118.02, 147.2, 150.3, 187.8; 5-(hydroxymethyl)furfural (HMF, 2) (0.082 g, 5%), $^1$H NMR ($CDCl_3$); 3.51 (brs, 1H), 4.66 (s, 2H), 6.50 (d, 1H), 7.21 (d, 1H), 9.51 (s, 1H), $^{13}$C NMR ($CDCl_3$); 56.9, 110.1, 123.9, 151.8, 162.0, 178.1; and levulinic acid (LA, 4) (0.011 g, 1%), $^1$H NMR ($CDCl_3$); 2.17 (s, 3H), 2.59 (t, 2H), 2.73 (t, 2H), $^{13}$C NMR ($CDCl_3$); 27.9, 29.9, 37.8, 178.2, 207.0. Filtration of the remaining aqueous layer gave a fine, black humic material (0.10 g).

The above procedure was used for a variety of materials, as shown in Table 2 below. Filter paper and cotton, which are nearly pure cellulose, provided high yields of CMF and the related, minor products (such as HMF, HAF and LA). As the cellulose content of the substrate decreases so did the mass yields of CMF, HMF, 2-(2-hydroxyacetyl)furan (HAF, 3) and levulinic acid (LA, 4).

TABLE 2

Yields of products (g) from 10 g of cellulose and biomass substrates.

| substrate | crude oil | CMF | HMF | HAF | LA |
| --- | --- | --- | --- | --- | --- |
| cellulose | 7.54 | 6.33 (71%) | 0.42 (8%) | 0.60 (7%) | 0.06 (3%) |
| filter paper | 7.22 | 6.08 | 0.39 | 0.42 | 0.13 |
| cotton | 7.20 | 5.97 | 0.32 | 0.51 | 0.10 |
| newsprint | 5.95 | 4.31 | 0.40 | 0.39 | 0.30 |
| wood$^a$ | 4.47 | 2.61 | 0.14 | 0.26 | 0.16 |
| corn stover | 4.30 | 2.64 (71.6%) | 0.10 (3.2%) | 0.29 (9.1%) | 0.16 (5.5%) |
| straw | 3.63 | 2.06 | 0.10 | 0.19 | 0.13 |

$^a$Birch (*Betula* sp.)

It is useful to compare the chemical yield of CMF, HMF, HAF and LA from raw biomass with the yield of products from pure cellulose, which is known to be 85% (*Angewandte Chem. Int. Ed.* 2008, 47, 7924). Determination of these yields requires a knowledge of the total hexose content of the substrate in question. Using a sample of biomass (corn stover) of known composition from the U.S. Department of Energy's National Renewable Energy Laboratory (NREL), the sample analyzed was found to contain 33.9% cellulose, 6.2% sucrose, and 1.5% galactan (w/w, dry basis) for a total hexose fraction of 41.6%. Applying this data to the above results for corn stover, the chemical yields were CMF, 71.6%; HMF, 3.2%; HAF, 9.1%; and LA, 5.5%, for a total yield of 89%, which is consistent with that of pure cellulose itself. This means that the conversion process is unaffected by the presence of the other components in raw biomass.

Furfural (7) can also be prepared when the starting saccharide contains pentose sugars. Table 3 gives the mass yields of furfural per 10 g of starting material, as well as the chemical yield for corn stover, which had a total of 27.2% pentosan content (24.1% xylan and 3.1% arabinan (w/w, dry basis). For comparison, the yield of furfural from pure xylose under the same conditions was also determined. The yield of furfural from xylose (67.5%), as well as the yield of 7 from the hemicellulose in corn stover (40.3%), is lower than that of 1-4 from glucose.

TABLE 3

Yields of furfural (g) from 10 g xylose and biomass substrates.

| substrate | furfural (7) | % yield |
| --- | --- | --- |
| xylose | 4.32 | 67.5 |
| newsprint | 0.29 | — |
| wood$^a$ | 0.74 | — |
| corn stover | 0.80 | 40.3 |
| straw | 0.71 | — |

$^a$Birch (*Betula* sp.)

Example 3

Conversion of Glucose into Furanic Products

Using the general procedure described in Example 2, glucose (2.01 g) gave crude product (1.425 g) which was chromatographed to give 5-(chloromethyl)furfural (CMF, 1) (1.145 g, 71%), 2-(2-hydroxyacetyl)furan (HAF, 3) (0.103 g, 7%), 5-(hydroxymethyl)furfural (HMF, 2) (0.116 g, 8%), levulinic acid (LA, 4) (0.032 g, 3%), and humic material (0.090 g).

Example 4

Conversion of Sucrose into Furanic Products

Using the general procedure described in Example 2, sucrose (2.06 g) gave crude product (1.543 g) which was chromatographed to give 5-(chloromethyl)furfural (CMF, 1) (1.322 g, 76%), 2-(2-hydroxyacetyl)furan (HAF, 3) (0.090 g, 6%), 5-(hydroxymethyl)furfural (HMF, 2) (0.055 g, 4%), levulinic acid (LA, 4) (0.064 g, 5%), and humic material (0.070 g).

Example 5

Preparation of 5-(Ethoxymethyl)furfural (5)

5-(Chloromethyl)furfural (CMF, 1) (1.24 g, 8.58 mmol) was dissolved in absolute ethanol (60 mL) and the solution was stirred at room temperature for 8 h. The excess ethanol was recovered by distillation and the residue was chromatographed (silica gel, $CH_2Cl_2:Et_2O$, 2:1) to give EMF (5) (1.26 g, 95%) as a pale yellow liquid, $^1H$ NMR ($CDCl_3$); 1.04 (t, 3H), 3.39 (q, 2H), 4.32 (s, 2H), 6.34 (d, 1H), 7.06 (d, 1H), 9.40 (s, 1H), $^{13}C$ NMR ($CDCl_3$); 14.1, 63.6, 65.3, 110.3, 121.8, 151.8, 157.9, 176.7.

Example 6

Preparation of 5-Methylfurfural (6)

The method of Hamada, et al. (K. Hamada, G. Suzukamo, K. Fujisawa, *Eur. Pat. Appl.* 1982, 44186A1) was used. A mixture of 5-(chloromethyl) furfural (CMF, 1) (1.17 g, 8.09 mmol) and $PdCl_2$ (0.030 g) in N,N-dimethylformamide (5 mL) was introduced into a flask which was evacuated, back filled with hydrogen, and kept under a positive pressure of hydrogen with a balloon. The reaction mixture was stirred at 40° C. for 3 h and then filtered through Celite. $CH_2Cl_2$ (150 mL) was added to the filtrate and the resulting solution was washed with 1M HCl (50 mL), 5% aq. $NaHCO_3$ (50 mL), and finally water (50 mL). The organic layer was dried over anhydrous $MgSO_4$. Evaporation of solvent and chromatography (silica gel, $CH_2Cl_2:Et_2O$, 2:1) gave MF (6) (0.78 g, 87%) as a colorless liquid, $^1H$ NMR ($CDCl_3$); 2.45, (s, 3H), 6.08 (d, 1H), 7.22 (d, 1H), 9.56 (s, 1H), $^{13}C$ NMR ($CDCl_3$); 14.0, 110.2, 124.4, 151.9, 159.8, 176.8.

Example 7

Preparation of CMF without Continuous Extraction

A 1 L round bottomed flask was charged with conc. HCl (80 mL), LiCl (6 g), 1,2-dichloroethane (500 mL), and microcrystalline cellulose (2.00 g, 12.3 mmol). The biphasic mixture was heated at 65° C. under fast mechanical stirring for 19 hours. The mixture was filtered and the organic layer was separated and dried over $MgSO_4$. Evaporation of the solvent gave CMF (1, 0.561 g, 31%).

Example 8

Preparation of HMF from CMF

CMF (1, 0.949 g, 6.56 mmol) was added in one portion to boiling water (900 mL) with fast stirring. After 25 sec the reaction was cooled to room temperature in an ice/water bath. The mixture was extracted with ethyl acetate (5×100 mL). Sodium chloride was added to the point of saturation and extraction with ethyl acetate was continued (5×100 mL). The combined extracts were dried over $MgSO_4$ and the solvent was evaporated. Column chromatography (silica, $Et_2O$:$CH_2Cl_2$, 1:1) gave HMF (2, 0.714 g, 86%) and LA (4, 0.075 g, 10%).

Example 9

Preparation of LA from CMF

A mixture of CMF (1, 2.701 g, 18.68 mmol), conc HCl (17.1 g, 173 mmol) and water (80 mL) was heated in a sealed vessel at 190° C. for 20 min. After cooling, the reaction mixture was filtered and then extracted with ethyl acetate (5×100 mL). Sodium chloride was added to the point of saturation and extraction with ethyl acetate was continued (5×00 mL). The combined extracts were dried over $MgSO_4$ and the solvent was evaporated to give pure LA (4, 2.010 g, 93%).

Example 10

Preparation of Ethyl Levulinate from CMF

A mixture of CMF (1, 3.166 g, 21.90 mmol) and absolute EtOH (80 mL) was heated in a sealed vessel at 160° C. for 30 min. The mixture was cooled to room temperature and the solvent was evaporated. The resulting crude product was chromatographed (silica, hexane:ethyl acetate, 1:1) yielding ethyl levulinate (2.675 g, 85%).

Example 11

Preparation of n-Butyl Levulinate and n-Butyl Formate from CMF

A mixture of CMF (1, 9.221 g, 63.79 mmol) and n-BuOH (50 mL) was heated at 110° C. for 2 hours. Distillation between 104-110° C. gave a mixture of n-butyl formate (5.649 g, 87%) and recovered n-BuOH (16.40 g). Distillation of the residue at 90-91° C./2 mm gave n-butyl levulinate (9.277 g, 84%).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for preparing 5-(chloromethyl)furfural (CMF), or a derivative thereof, in greater than 50% yield, the method comprising:

(a) contacting a polysaccharide, an aqueous acid and an organic solvent in a reaction vessel at a temperature of from about 30° C. to about 100° C., such that CMF is produced;

(b) removing the organic solvent to an isolation vessel, such that any CMF dissolved in the removed organic solvent is collected in the isolation vessel; and (c) adding additional organic solvent to the reaction vessel, wherein steps (b) and (c) are performed continuously, thereby preparing CMF, or a derivative thereof, in greater than 50% yield from the polysaccharide.

2. The method of claim 1, wherein the polysaccharide is selected from at least one member of the group consisting of cellulose, hemicellulose and lignocellulose.

3. The method of claim 1, wherein the polysaccharide comprises cellulose.

4. The method of claim 1, wherein the aqueous acid is hydrochloric acid.

5. The method of claim 1, wherein the contacting step further comprises an inorganic salt in the reaction vessel.

6. The method of claim 1, wherein the organic solvent is more dense than water.

7. The method of claim 1, wherein the organic solvent is less dense than water.

8. The method of claim 1, wherein the organic solvent is 1,2-dichloroethane (DCE).

9. The method of claim 1, wherein the temperature is from about 60° C. to about 70° C.

10. The method of claim 1, wherein the organic solvent removed to the isolation vessel is added to the reaction vessel as the additional organic solvent, such that CMF in the isolation vessel remains in the isolation vessel.

11. The method of claim 1, wherein the method also prepares furfural.

12. The method of claim 1, wherein the method also prepares 5-(hydroxymethyl)furfural (HMF), 2-(2-hydroxyacetyl)furan (HAF) and levulinic acid (LA) such that the total yield of CMF, HMF, HAF and LA is at least 75% based on the saccharide.

13. A method for preparing 5-(chloromethyl)furfural (CMF), or a derivative thereof, in greater than 50% yield, the method comprising:

(a) contacting cellulose, concentrated hydrochloric acid and 1,2-dichloroethane in a reaction vessel at a temperature of about 65° C., such that a biphasic mixture is formed with the cellulose and concentrated hydrochloric acid forming an aqueous layer and the 1,2-dichloroethane forming an organic layer, wherein CMF is produced;

(b) removing the 1,2-dichloroethane to an isolation vessel, such that any CMF dissolved in the removed 1,2-dichloroethane is collected in the isolation vessel; and (c) adding the removed 1,2-dichloroethane to the reaction vessel, such that the CMF in the isolation vessel remains in the isolation vessel, wherein steps (a), (b) and (c) are performed continuously, thereby preparing CMF, or a derivative thereof, in greater than 50% yield from the cellulose.

14. The method of claim 5, wherein the inorganic salt is lithium chloride.

15. The method of claim 1, wherein the contacting step is performed at a pressure of from about 0.1 to about 10 atm.

16. The method of claim 1, wherein the contacting step is performed at a pressure of from about 1 to about 10 atm.

* * * * *